United States Patent
Zimmermann et al.

(10) Patent No.: US 7,553,452 B2
(45) Date of Patent: Jun. 30, 2009

(54) PROCEDURE FOR CHANNEL ADJUSTMENT OF A MULTI-CHANNEL METERING APPARATUS

(75) Inventors: Peter Zimmermann, Kahla (DE); Torsten Rausch, Jena (DE); Gerd Heiβe, Jena (DE); Hartmut Köberich, Kahla (DE); Simon Renard, Jena (DE); Thomas Moore, Drackendorf (DE); Wolfgang Krämer, Jena (DE)

(73) Assignee: CyBio AG, Jena (DE)

( * ) Notice: Subject to any disclaimer, the term of this patent is extended or adjusted under 35 U.S.C. 154(b) by 866 days.

(21) Appl. No.: 10/722,113

(22) Filed: Nov. 25, 2003

(65) Prior Publication Data

US 2005/0035146 A1    Feb. 17, 2005

(30) Foreign Application Priority Data

Nov. 26, 2002    (DE) .............................. 102 55 595

(51) Int. Cl.
*B01L 3/02* (2006.01)

(52) U.S. Cl. .................. 422/100; 422/99; 422/101; 222/55; 436/180

(58) Field of Classification Search ........... 422/99–101; 222/55; 436/180
See application file for complete search history.

(56) References Cited

U.S. PATENT DOCUMENTS

| RE35,010 E * | 8/1995 | Price ........................... 222/1 |
|---|---|---|
| 5,441,204 A | 8/1995 | Tappel et al. |
| 5,741,554 A | 4/1998 | Tisone |
| 5,743,960 A | 4/1998 | Tisone |
| 5,916,524 A | 6/1999 | Tisone |
| 6,063,339 A | 5/2000 | Tisone et al. |
| 6,576,295 B2 | 6/2003 | Tisone |
| 6,615,638 B1 | 9/2003 | Lochner et al. .............. 73/1.74 |
| RE38,281 E | 10/2003 | Tisone |
| 2002/0001675 A1 | 1/2002 | Tisone |
| 2002/0064482 A1 | 5/2002 | Tisone et al. |
| 2002/0124627 A1 | 9/2002 | Luchinger .................. 73/1.74 |
| 2002/0159919 A1 | 10/2002 | Churchill et al. |
| 2004/0020938 A1 | 2/2004 | Boillat et al. |

FOREIGN PATENT DOCUMENTS

| EP | 0 810 438 | 12/1997 |
|---|---|---|
| EP | 1 036 594 A2 | 9/2000 |
| EP | 1 099 480 A2 | 5/2001 |
| JP | 2000-258438 | 9/2000 |
| WO | WO 00/01798 | 1/2000 |
| WO | WO 02/33423 | 4/2002 |

OTHER PUBLICATIONS

European Search Report for European Patent Application Serial No. EP 03 02 7083.9, dated Jul. 25, 2005, 3 pgs.

* cited by examiner

*Primary Examiner*—Jill Warden
*Assistant Examiner*—Jyoti Nagpaul
(74) *Attorney, Agent, or Firm*—Reed Smith LLP

(57) ABSTRACT

Procedure for equilibration of the delivery volumes of a multi-channel metering apparatus with an arrangement of independently controlled dispensing channels 1.1-1.n, delivering individual volumes of dispensing fluid to cavities 3.1.1-3.n.n, where measured values relevant to the individual delivery volumes are measured for the same control value and from which an adjustment value is specified with a tolerance band and the control value is adjusted for dispensing channels 1.1-1.n, the measured values of which lie outside the tolerance band. The invention also applies to an apparatus for implementing the procedure.

8 Claims, 1 Drawing Sheet

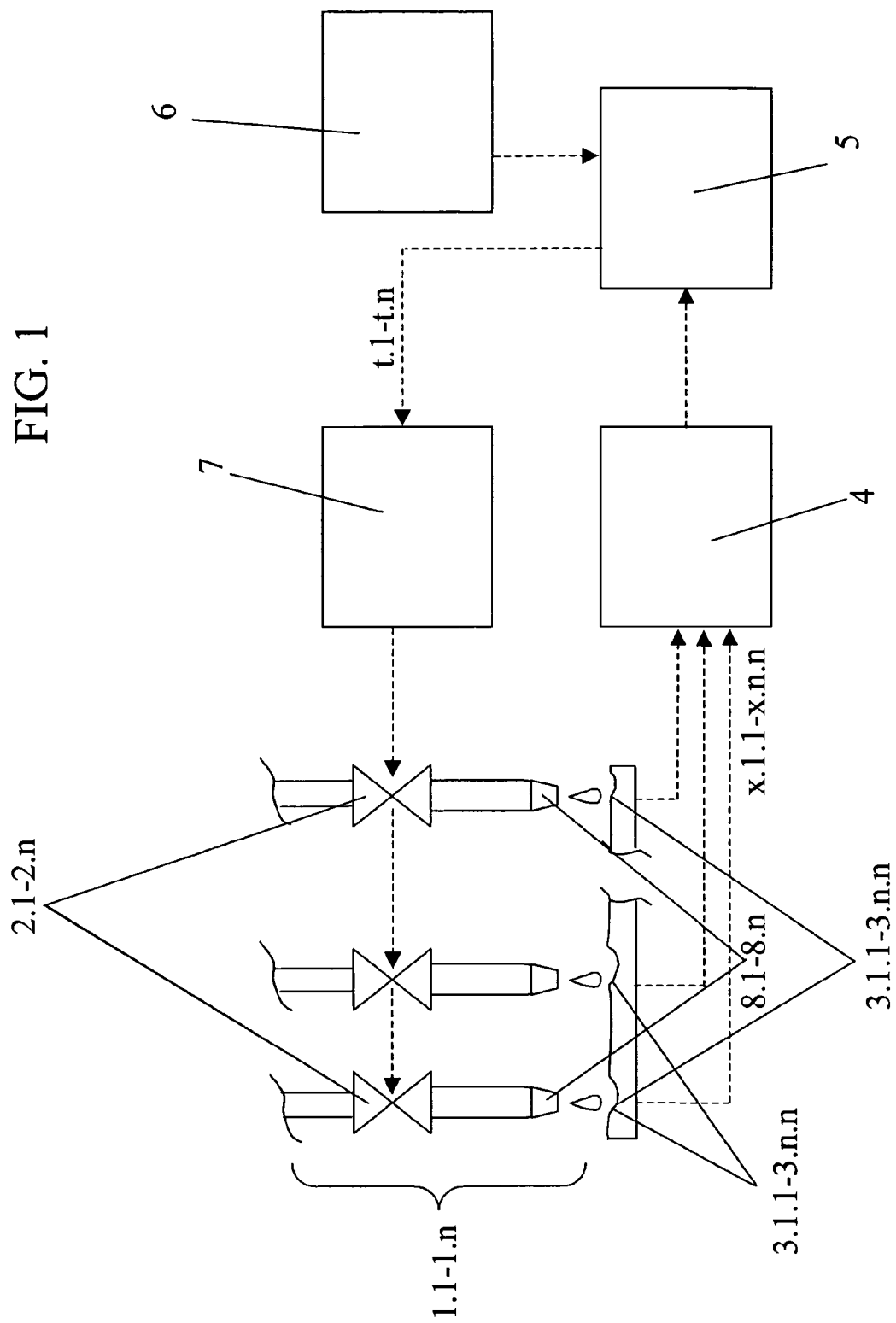

PROCEDURE FOR CHANNEL ADJUSTMENT OF A MULTI-CHANNEL METERING APPARATUS

For multi-channel metering apparatuses which are primarily employed today in fully automatic laboratory equipment in pharmacological, molecular-biological, biochemical and chemical research, the constant task in principle is to deliver numerous tiny volumes (tests) of fluid reagents (dispensing fluid) precisely proportioned onto a carrier, e.g. a micro titration plate, in the shortest possible time in both localized and quantitative terms. The quantitatively precise dosage correspondingly represents an essential performance feature for multi-channel metering apparatuses. In order to obtain a small volume fluctuation range and thus a small coefficient of variation different measures are taken for generically similar devices from the state of the art.

In contrast to comparable devices for printing, where in principle only a single defined volume of a defined fluid is delivered, multi-channel metering apparatuses are also supposed to be suitable for dispensing fluids of different physical properties, such as viscosity or to provide samples from tests of different dispensing fluids and/or volumes.

Generically similar metering apparatuses differ, among other things, in the way in which the dispensing fluid reaches the respective discharge opening of a dispensing channel (tip and/or nozzle) and the technical means with which proportioned delivery is effected.

With regard to intake of the dispensing fluid, known devices are divided into those where the dispensing fluid is suctioned in (pick up dispenser) via the discharge opening (from the front) and those with which the dispensing fluid is conveyed to the discharge opening from the rear (bulk reagent dispenser). For the purpose of differentiation the discharge opening in the case of pick up dispensers shall be designated as the tip and nozzle in the case of bulk reagent dispensers.

If one divides the known devices according to the means with which a proportioned delivery is effected, then there should first be a fundamental differentiation made between technical solutions where delivery can only be controlled over all tips/nozzles (manifold systems) and those with which the delivery of each individual tip/nozzle may be controlled (multi-single-channel systems).

In order to be able to simultaneously deliver a uniform volume over all nozzles with a manifold system, different distributor structures are known in particular from the state of the art with which the dispensing fluid is supposed to be evenly distributed to the nozzles from a common storage vessel. Such distributor structures are disclosed for example in U.S. Pat. No. 5,441,204 and in EP 1 036 594. Even delivery of the drops is realized in U.S. Pat. No. 5,441,204 through an electrostatic principle in that the continuously conveyed fluid is electro-statically charged and released from the surface of the tip by an electrical field. In EP 1 036 594 the fluid is carried at a high speed to the discharge openings via a flexible connection and a distributor. With an abrupt stop of the fluid flow which briefly exists due to the inertia, thus providing for contraction of the flexible connection, the jet breaks off due to the high kinetic energy, ostensibly without forming a drop. Fluid remainders are withdrawn from the discharge openings with easing of the connection.

These technical solutions necessarily presuppose that all of the nozzles are fed from a common storage vessel, whereby only the same dispensing fluid may be delivered over all of the nozzles. Thus there is no possibility of providing a test sample of different dispensing fluids and no differentiation may be made in the delivery quantity of the nozzles among themselves. The fluctuation range in fluid quantities delivered through individual nozzles is determined by the design and manufacturing tolerances and cannot be influenced in terms of control.

In the case of multi-single-channel systems, however, delivery of each individual tip or nozzle can be controlled.

In patent application WO 00/01798 a multi-channel metering apparatus is described with which all of the nozzles can be filled from both a common and from different storage vessels and with which different volumes can also be delivered. The individual nozzles respectively form independent dispensing channels in relation to each other with a syringe pump, a flexible connection and a valve. An additional volume which expands and thus effects overpressure in the connection closed at the other end by means of the valve is introduced into the flexible connection filled with dispensing fluid via the defined stroke of the syringe pump. Precisely this additional volume is delivered with opening of the valve, i.e. the volume delivered by the nozzles is controlled by the stroke.

A metering apparatus with a pressure pump and a conventional valve is described in U.S. Pat. No. 5,741,554. The pressure pump, a syringe pump filled with dispensing fluid, is connected with the end of a hose at the other end of which a solenoid valve is arranged near the nozzle. The motor-driven piston of the syringe pump is powered with a defined speed which determines the flow rate. Together with the frequency of the valve it determines the dispensed volume. If, for example, the pump produces a flow rate of 1 µl/s and the frequency of the opening/closing cycle of the valve amounts to 100 per second, then the droplet size is 10 nl. Thus the dispensed volume is controlled via the piston stroke speed and the valve opening frequency.

The basic principles described for dosage of the dispensing volume, namely via path (stroke of the syringe pump) and/or a time (opening time of the valve) can be verified with numerous further descriptions.

This equipment may be assumed to be calibrated inasmuch as a particular path/time sequence is correlated with a desired fluid delivery volume (target volume) via internally memorized measurement curves, or gradients. Since, however, a gradient—a function of volume path/time sequence—is not always a linear curve, the established path/time sequence for a particular target volume can be subject to error, resulting in a fluctuation range for real delivery volumes which straddles the actual target value.

With all of these technical solutions it is a constant task to keep the coefficient of variation (CV) (deviation of the individual dispensing volumes from their average value) of the individual dispenser (dispensing channel) as small as possible. Coefficients of variation of less than 2% with a delivery volume of 500 nl and less than 5% with 50 nl are achieved. As a rule, manufacturers do not indicate a coefficient of variation based on the average value of all of the individual dispensers (dispensing channels). This alone will already be substantially larger due to the mechanical tolerances of the dispensing channels in relation to each other.

In patent application WO 02/33423 a dispensing apparatus is described with which the dispensing volume of each dispensing channel is respectively regulated via the opening time of the pertinent valve. In the individual dispensing channels means are provided for measuring the volume flow rate (flow sensors) as well as electronic means which control the valve in reaction to the measured values of the flow sensors. An 8-channel dispensing apparatus, offered by the patent applicant, which is based on the technical solution protected here promises a coefficient of variation CV of less than 5%

(based on the average value over all of the dispensing channels) for a delivery volume in the range of 50 nl-10 µµl.

An advantage in contrast to the other indicated solutions is that the dispensing volume of all of the dispensing channels is not determined by controlling a specific time or path, but rather the volume flow rate serves as a controlled variable for the opening times of the respective individually assigned valve. Any tolerances capable of having an impact on the dosing volumes up to the flow sensor do not influence the coefficient of variation and therefore on the tolerances of the dispensing volumes forming a test sample.

Tolerances on the basis of flow sensor measurement errors and droplet forming, creep and vaporization at the nozzles are not excluded, nor can tolerances resulting from the oscillating quantities of individual equipment components in contact with the dispensing fluid as well as the oscillating quantities and inertia of the dispensing volumes be completely ruled out.

The object of the invention is to create a procedure with which the individually controlled dispensing channels of a multi-channel metering apparatus can be more accurately adjusted.

A further object of the invention is to create a multi-channel metering apparatus which is suitable for automatic implementation of the procedure.

Furthermore, the procedure should allow the operator of the multi-channel metering apparatus to make use of it any number of times over the period of the latter's useful life.

These tasks are solved according to the invention with the characteristics of claims 1 and 4.

Advantageous embodiments are described in the dependant claims.

Any equipment impact on the delivery volume is rule out by adjustment of the valve opening times as a function of the volume of dispensing fluid delivered by the pertinent dispensing channel.

Adjustment may cover a target volume (calibration) or a statistically determined measured value such as, for example, a median or mean value for the actual delivery volumes of the individual dispensing channels (equilibration).

The dispensing channels can be adjusted for various dispensing fluids under various ambient conditions; thus fluctuations in the delivery volumes can be reduced for different fluids and under different ambient conditions.

Controlling the valve opening times as a function of the actually dispensed volumes presupposes the availability of a measuring device to measure values which may be assigned to the fluid volumes dispensed to individual cavities.

As a rule, the photometric and gravimetric measurement method is known to serve this purpose. In the case of the gravimetric method the mass of the delivery volume is determined by weighing and converted in terms of volume by means of the density. Appropriate measuring apparatuses are known to the expert.

One frequently applied photometric method of measurement is based on the recording of light absorption in a homogeneous dye solution. A dye solution with a known dye concentration, the volume of which is to be determined, is dispensed into a basic fluid of known volume and known absorption capacity. The dye concentration of the mix, and by extension the volume of the added dye solution, can be determined on the basis of the subsequently measured absorption. Other photometric measuring methods are based on recording the fluid fluorescence or luminescence of the fluid. Appropriate measuring apparatuses to this end are also known to the expert.

Since the subject of the invention concerns neither the measuring methods for determining the volume of a fluid nor the appropriate measuring apparatus, no further details shall be provided. A measuring device, the existence of which represents an essential characteristic of the invention, is understood to mean any measuring apparatuses which are suitable for measuring the relevant measured values for a respective fluid volume.

The device is usefully incorporated into multi-channel metering apparatus, especially if it is a reader for photometric acquisition of measured data or incorporated into the calibration method as accessory equipment. Values thus recorded can be conveyed to a computer unit in the multi-channel metering apparatus via data line, data carrier or manual input. The adjustment process varies depending on whether the dispensing channels of the multi-channel metering apparatus should be aligned to a single volume, volume range or different fluids and under different ambient conditions.

Within the meaning of the invention the term "alignment" should always be used if both "calibration" and "equilibration" may be intended.

Calibration within the meaning of the invention is the adjustment of the individual dispensing channels to one or more target values. The target values may be volumetric or related values.

Equilibration is the adjustment the of dispensing channels to each other through adjustment of the delivery volumes.

In the following the invention shall be described in greater detail on the basis of a drawing of an embodiment.

FIG. 1 shows a block circuit diagram for an apparatus according to the invention.

The block circuit diagram shown in FIG. 1 shall be limited to units of essential importance for the description of the invention. The multi-channel metering apparatus incorporates an arrangement of individual dispensing channels 1.1-1.n which when valves 2.1-2.n are open each deliver a dispensing fluid into individual cavities 3.1.1-3.n.n via a nozzle 8.1-8.n. A measuring device 4 is arranged at cavities 3.1.1-3.n.n so as to simultaneously or consecutively measure values for individual volumes of fluid dispensed into cavities 3.1.1-3.n.n which—as already explained—may, for example, be mass, absorption, fluorescence or luminescence. Measuring device 4 is connected to an input of computer unit 5 while there is a data input unit 6 at the second input of the computer unit. The output of which is connected to a control unit 7. Control unit 7 is connected on the output side to valve control inputs 2.1-2.n.

The delivery volume of the individual dispensing channels 1.1-1.n is effected in the work process via control of the opening time t.1-t.n of the individual valves 2.1-2.n. In order to control valves 2.1-2.n for the work process in terms of the dispensing channels, the multi-channel metering apparatus shall be adjusted prior to the initial work process. This may also be repeated by the operator at various intervals at the actual workplace.

A particularly advantageous application of the adjustment procedure according to the invention is described in the following. Here adjustment is to be effected through equilibration.

For the equilibration of all of the dispensing channels 1.1-1.n all of the valves 2.1-2.n are opened simultaneously for the same length of time t.1-t.8 in which the channels, which are arranged in fixed order, dispense fluid into a correlated arrangement of cavities 3.1.1-3.n.n. To enable a sufficiently accurate mean value to be established for the individual dispensing channels, e.g. for equilibrating an 8-channel metering apparatus (n=8), a 384 type micro-titration plate is filled, i.e. each dispensing channel 1.1-1.8 fills 48 cavities. In spite of the same opening time length t.1-t.8, which is not necessarily uninterrupted, neither do dispensing channels 1.1-1.8 deliver precisely the same volume over the 48 deliveries, nor is the volume delivered by dispensing channels 1.1-1.8 identical in relation to each other, which is established in particular by the mechanical and fluid tolerances of the dispensing channels among each other. With the help of a measuring device 4 as known to the expert, 384 volumetric measurement values x.1.1-x.48.48 are measured and respectively assigned to the opening time length t and a dispensing channel 1.1-1.8. A mean value x.1-x.8 (which may also be a median value) is established on the basis of the 48 values assigned to a respective channel and is stored (storage data groups) with the length of the opening time length t, assigned to a dispensing channel 1.1-1.8.

Now in order to align dispensing channels 1.1-1.8 in relation to each other, a median value to which the dispensing channels are adjusted is formed from the mean values x.1-x.8. The median value is a value which is exceeded and undershot with equal frequency by the underlying measured values, here the mean values x.1-x.8.

Underlying the principle of adjustment to a median value is the knowledge that it is much less a matter of the individual dispensing channels 1.1-1.8 delivering a certain target volume than keeping the range of fluctuation of the delivered volumes in relation to each other as low as possible.

While the length of opening time t.1-t.8 of valves 2.1-2.8 derived from the storage data groups are adjusted for a target volume for calibrating dispensing channels 1.1-1.8-which is usually required for all of the dispensing channels—the opening time length t.1-t.8 of valves 2.1-2.8 in the case of equilibration of the dispensing channels from the storage data is adjusted for the median value. If a certain margin of fluctuation (median band), for example 2%, is left around the median value, the length of the opening time t.1-t.8 does not need to be adjusted for every dispensing channel. The fewer the adjustments which need to be made, the less errors occur with actual delivery.

Thus the fluctuation range in the actual delivery of the dispensing channels 1.1-1.8 is smaller in the case of equilibration than in the case of calibration. While alignment to an actual statistical mean value is just as conceivable, the length of the opening time Δt needs to be adjusted for a greater number of dispensing channels 1.1-1.8.

Adjusting opening time t.1-t.8 in terms of the valve means that, depending on whether the particular mean value x.1-x.8 of individual dispensing channels 1.1-1.n is above or below the median band, opening time Δt is reduced or extended for the respective dispensing channel 1.1-1.n.

The entire operation may be repeated in order to check whether all of the mean values x.1-x.8 are now within the median band as a result of the adjustments. A narrower or wider median band may be selected if the values are left unadjusted, depending on the desired margin of fluctuation.

If the multi-channel-metering apparatus is equilibrated to only one volume, then a stop may be made at this point. The final storage data groups which respectively assign a volume V to a length of opening time t.1-t.8 and a dispensing channel 1.1-1.n are stored in computer unit 5.

If all of the dispensing channels 1.1-1.n are now to deliver this volume for the work process of the multi-channel metering apparatus, then the length of the opening time t.1-t.8 of the individual valves 2.1-2.n is individually controlled in accordance with the stored storage data groups. The volumes delivered are then within the median band.

If other volumes are now to be dispensed during the work process or where the dispensing channels 1.1-1.n deliver different volumes, then computer unit 5 calculates an appropriate opening time t.1-t.8 for dispensing channels 1.1-1.8 from the storage data groups. It is obvious that the coefficient of variation over the dispensing channels is now greater than for delivery of the adjusted volume since the volume-time characteristic curves for the individual dispensing channels 1.1-1.8 show inconstancies which a computer calculation fails to take into account.

A multi-channel metering apparatus that is intended for delivery of different volumes of fluid from the outset is thus equilibrated for a volume range.

To this end equilibration, such as already described for a single volume, is carried out on several volumes (sampling points) and several storage data groups are then stored on computer unit 5 for individual dispensing channels 1.1-1.8.

On the basis of the storage data groups measurement curves can be formed across a range of volumes which more closely approximate the actual delivery performance of individual dispensing channels 1.1-1.8 than when a straight line is specified with a measuring point and the zero point. The more sampling points a gradient has the more accurate it is, i.e. the higher the expenditure, the greater the accuracy.

Storage data groups can be enlarged by the values of further parameters, such as pressure, temperature or viscosity of the dispensing fluid. Computer unit 5 then creates measured curves which not only assign volumetric values to an opening time Δt for each dispensing channel 1.1-1.8, but also a dispensing fluid, operating temperature or pressure under which the dispensing fluid stands. The fluctuation range for the actual volumes delivered is reduced even further if such relevant measured curves of this type can be used to measure the control value for individual valves for control purposes.

The procedure according to the invention is not confined to the control of delivered volumes for individual dispensing channels 1.1-1.n over the length of opening time Δt of valves n2.1-2.n but can also be applied if the volume delivered is effected by other technical means, e.g. a controlled plunger stroke.

The procedure can also be applied for adjustment of a regulated fluid delivery. Errors due to flow sensor tolerances, for example, can be corrected in the case of an apparatus where a specific control variable is formed to regulate the length of opening time for the individual valves, for example by means of a flow sensor in each dispensing channel.

The expert in this field will conclude that the invention is not limited to the specifics of the embodiments described by way of example, but rather that the present invention may be embodied in other special forms without deviating from the scope of the invention specified in the enclosed claims.

List of the Reference Symbols Used
1.1-1.n Dispensing channels
2.1-2.n Valves
3.1.1-3.n.n Cavity
x.1.1-x.n.n Mean value
4 Measuring device
5 Computer unit
6 Data input unit
7 Control unit
8.1-8.n Nozzle
t.1-t.n Length of opening time

The invention claimed is:

1. A process for adjusting the fluid delivery volumes of a multi-channel metering apparatus with an arrangement of independently controlled dispensing channels 1.1-1.n delivering individual volumes of dispensing fluid to cavities 3.1.1-3.n.n, the process comprising the following procedural steps:

delivering individual volumes of dispensing fluid via dispensing channels 1.1-1.n, where the delivery is controlled by a control value that is the same for all the dispensing channels;

measuring a value relevant to the individual volumes delivered;

correlating the measurement values with the control value and the particular dispensing channel 1.1-1.n;

statistically determining an equilibration value from all the measurement values;

determining a permissible band of tolerance for the equilibration value;

adjusting up or down the control value of any dispensing channel whose measurement value is above or below the band of tolerance for the equilibration value;

memorizing control values and measurement values as data storage groups.

2. The process of claim 1, wherein the process further comprises:

determining the mean value of the measurement values for each of the dispensing channels 1.1-1.n correlating each of the mean values with the control value and the particular dispensing channel.

3. The process of claim 2, wherein the equilibration value is the median value of the mean values for each of the dispensing channels 1.1-1.n.

4. The process of claim 1, wherein the equilibration value is the mean value of the measurement values.

5. The process of claim 1, wherein the control value is opening times t.1-t.n for valves 2.1-2.n arranged in each of the dispensing channels 1.1-1.n.

6. The process of claim 1, wherein the control value is the plunger stroke of the pump connected to each of the dispensing channels 1.1-1.n.

7. The process of claim 1, wherein the steps of the process are completed many times in sequence in order to align dispensing channels 1.1-1.n on more than one delivery volume or tolerance band.

8. The process of claim 1, wherein further storage data such as dispensing fluid pressure, temperature and viscosity are added to the storage data groups.

\* \* \* \* \*